United States Patent [19]

Prevedello et al.

[11] 4,409,419

[45] Oct. 11, 1983

[54] PROCESS FOR PREPARING 2,5-DIMETHYL-2,4-HEXADIENE

[75] Inventors: Aldo Prevedello; Edoardo Platone; Morello Morelli, all of San Donato Milanese, Italy

[73] Assignee: Anic S.p.A., Palermo, Italy

[21] Appl. No.: 290,655

[22] Filed: Aug. 6, 1981

[30] Foreign Application Priority Data

Aug. 29, 1980 [IT] Italy ............................... 24353 A/80

[51] Int. Cl.³ .......................... C07C 1/20; C07C 1/253
[52] U.S. Cl. ..................................... 585/611; 585/610
[58] Field of Search ................................ 585/610, 611

[56] References Cited

U.S. PATENT DOCUMENTS

| | | | |
|---|---|---|---|
| 1,002,399 | 9/1911 | Hofmann et al. | 585/610 |
| 1,179,408 | 4/1916 | Delbrück et al. | 585/610 |
| 1,923,569 | 8/1933 | Cunradi et al. | 585/611 |
| 1,944,153 | 1/1934 | Cunradi et al. | 585/611 |
| 2,310,809 | 2/1943 | Reppe et al. | 585/611 |
| 2,461,362 | 2/1949 | Young et al. | 585/610 |
| 2,715,649 | 8/1955 | Hammond | 585/611 |

*Primary Examiner*—Curtis R. Davis
*Attorney, Agent, or Firm*—Morgan, Finnegan, Pine, Foley & Lee

[57] ABSTRACT

2,5-Dimethyl-2,4-hexadiene is prepared by dehydrating 2,5-dimethyl-2,5-hexanediol in liquid phase. The reaction takes place by contacting 2,5-dimethyl-2,5-hexanediol, melted or dissolved in an appropriate solvent, with acids, heating the mixture at a temperature of 100° C.-160° C. and distilling off water from the reaction environment as it is being formed. The pressure can range between 1 and 10 bars.

7 Claims, No Drawings

PROCESS FOR PREPARING 2,5-DIMETHYL-2,4-HEXADIENE

BACKGROUND OF THE INVENTION

This invention relates to a process for the preparation of 2,5-dimethyl-2,4-hexadiene in the liquid phase starting from 2,5-dimethyl-2,5-hexanediol.

2,5-dimethyl-2,4-hexadiene is a product of great importance since it is an intermediate in the synthesis of pyrethroids.

A number of synthesizing methods for 2,5-dimethyl-2,4-hexadiene are known. Among these, the following can be mentioned:

(1) From 2,5-dibromo-2,5-dimethyl hexane, by elimination of hydrobromic acid;
(2) From 2,2,5,5-tetramethyl tetrahydrofuran, by heating in a sealed tube at 180° C.–190° C. with five times as much of 1% HCl;
(3) By isomerizing 2,5-dimethyl-1,5-hexadiene in the presence of alcoholic solutions of alkalies at 180° C.;
(b 4) From 1-bromo-2-methyl-1-propane, in the presence of sodium in benzene at 55° C.–65° C.;
(5) By isomerizing 2,5-dimethyl-1,5-hexadiene on alumina at 365° C. or on mixtures of $Cr_2O_3$–$Al_2O_3$ at 250° C.;
(6) From 2,5-dimethyl-1,5-hexadiene by heating to a boil with 4-toluene-sulphonic acid.

These methods are quite peculiar, have scanty importance from the commercial standpoint and are mainly adapted to laboratory-scale preparations.

There are also methods for preparing 2,5-dimethyl-2,4-hexadiene starting from 2,5-dimethyl-2,5-hexanediol (DHAD), which is the same starting compound as used in the method of the present invention.

Said methods, however, are cumbersome, expensive and poorly selective and comprise flowing DHAD over catalytic beds of alumina impregnated with orthophosporic acid, or deposited on alumina or admixtures of alumina and chromium trioxide, at temperatures of from 200° C. to 300° C.

Under such conditions, there can be formed, besides 2,5-dimethyl-2,4-hexadiene, other, undesirable, $C_8H_{14}$ isomers.

It is known, on the other hand, (see HOUBENWEYL, Methoden der organischen Chemie, Vol. VI/3, pages 528–535) than diols having the two hydroxyls separated by four carbon atoms, such as 2,5-dimethyl-2,5-hexanediol, easily form tetrahydrofurans by intramolecular cyclization with elimination of water.

More particularly, formation is disclosed in the literature (see W. REPPE, Annalen der Chemie, Vol. 596, page 110, (1955)) of 2,2,5,5-tetramethyl tetrahydrofuran by treating DHAD with aqueous solutions of phosphoric acid or potassium bisulphate under reflux conditions, or also with dilute sulfuric acid.

BRIEF STATEMENT OF THE INVENTION

It has been now quite surprisingly ascertained, in accordance with the present invention, that under particular conditions, DHAD (i.e. 2,5-dimethyl-2,5-hexanediol) forms in good yields and with good selectivity, 2,5-dimethyl-2,4-hexadiene, in the liquid phase and under conditions which are much blander than those which characterize the procedures enumerated above which employ the same starting compound.

The method according to the present invention is carried out by contacting 2,5-dimethyl-2,5-hexanediol, melted or dissolved in an appropriate solvent, with acids or aqueous solutions thereof, refluxing the mixture thus obtained and distilling off the water as it is being formed in the reaction environment, the organic products which are distilled off with water being recycled to the reaction mixture.

DESCRIPTION OF THE PREFERRED EMBODIMENTS

The reaction can be carried out both under atmospheric pressure and under positive pressures, up to a value of 10 bars; it is preferred, however, to work under ambient pressures and in an environment which is made inert by nitrogen, so as to prevent any possible polymerization of the diene concerned.

Under atmospheric pressure and positive pressures, the reaction temperature is in the range 100° C.–160° C., preferably 100° C.–140° C., consistent with the composition of the reaction mixture. Under these conditions the removal of an almost theoretical amount of water is experienced in times which may vary from a few minutes to a few hours, according to the concentration of the acid, the size of the reaction vessels and the temperature conditions.

The acids (or derivatives thereof, or substances capable of forming free acids) which can be used for the reaction of dehydration of DHAD may be selected from the group consisting of boric acid, hydrobromic acid, iodine, phosphorus pentoxide, potassium bisulphate, oxalic acid, phosphoric acid, polyphosphoric acid, and toluene sulphonic acid.

Best results have been achieved with derivatives of phosphoric acid, such as 85% phosphoric acid, 99% phosphoric acid, and polyphosphoric acid.

The ratio acid/DHAD is extremely critical to the effects on the reaction velocity.

In order that very short reaction times may be obtained, it has been found useful to employ the acid at a concentration ranging from 1% and 50% by weight relative to the DHAD, the preferred range being from 3% to 30%. The DHAD-dehydration reaction can be carried out with or without a solvent.

Where a solvent is employed it is preferably selected from those solvents which have a boiling temperature considerably above the boiling point of water, such as, for example, vaseline oil, decaline, cimene and the like.

Considering now the operative procedure in the greater detail, the reaction can be started in any of the following three ways:

(a) DHAD and the acid concerned are admixed in the cold, after which the reaction admixture is heated;
(b) the acid is added to the melted DHAD;
(c) the melted DHAD is added to the heated acid.

In all of these three cases, while operating under reflux conditions and at atmospheric pressures, the temperature of the reactor is self-adjusting as a consequence of the formation of the dehydration products, and the temperature being a function of the composition of the mixture as such.

In order to offset undesirable oligomerization reactions of 2,5-dimethyl-2,4-hexadiene, the reaction can be carried out in the presence of antioxidants such as 2,5-ditert.butyl hydroquinone, 2,6-ditert. butyl-4-methyl phenol, $\beta$, $\beta'$-bis-(2-hydroxy-3-tert. butyl-5-methyl-benzylthio) diethyl ether, 2,2'-methylene-bis (4-methyl-6-tert.butyl phenol), 4,4'-methylene bis (2,6-di-tert.butyl phenol), hydroquinone monomethylether and hydroquinone. On completion of the reaction, the raw product of the reaction is stripped of the phosphoric acid by decanting and dried, preferably on anhydrous sodium carbonate, to remove residual traces of acidity, filtered, and then fractionally distilled. Yields, conversions and selectivities are determined gas-chromatographically in, on the raw reaction product after filtering off the sodium carbonates the presence of an appropriate internal standard (m-xylene in the case in point). The by-products of the reaction consist predominantly of oligomers of dimethyl hexadiene and traces of tetramethyltetrahydrofuran and $C_8H_{14}$ isomers.

The reaction has been carefully studied by the present applicants for DHAD due to the high practical interest of 2,5-dimethyl-2,4-hexadiene. It is apparent however, that like behaviour is exhibited with alcohols having a like structure (1,4-di-tertiary diols) and thus with the present process, it is possible efficiently to prepare 2,5-diethyl-2,4-hexadiene, 2-ethyl-5-methyl-2,4-hexadiene, 2,5-biphenyl-2,4-hexadiene, tetraphenylbutadiene and the like.

EXAMPLE 1

A 250-ml flask having a magnetic stirrer, thermometer, Marcusson head with bubble condenser and electrical heater is charged with 68.2 grams of DHAD and 7.1 g (10.4% by wt relative to DHAD) of 85% phosphoric acid. Heat is applied to the admixture and, starting to count time from the beginning of condensation of the vapors, after about three hours an amount of water has distilled off which is slightly above the theoretical amount (2 mols $H_2O$ per mol DHAD), the excess being due to the water contained in the 85% phosphoric acid. Towards the end of the test, the phosphoric acid, which was initially completely soluble in the reaction mixture, separates from the mixture and forms a reddish oil.

The organic phase is physically separated from the phosphoric residue, dried on a small amount of anhydrous sodium carbonate and collected on a filter. The yield of 2,5-dimethyl-2,4-hexadiene is gas-chromatographically determined on an Apiezon L column having a height of 3 m at 130° C. and is 65% molar. The conversion of DHAD is 100% and the selectivity is 65%. The phosphoric residue is reused in subsequent test runs. There are added 68.5 grams (additional) of DHAD and heating is restarted. The same quantity of water as previously formed during three hours is now obtained slightly earlier (2 hours). The organic phase is separated again, 68.5 additional grams of DHAD are added to the oil which is left, heating is restarted once more, and after two hours the dehydration is virtually completed.

EXAMPLE 2

Using the same apparatus described in EXAMPLE 1, the flask is charged with 70.9 grams of DHAD and 3.6 grams (5.07% by wt, compared with 10.4% by wt in EX. 1) of 85% phosphoric acid. Heat is administered and after 7 hours there has distilled off only ⅔ of the theoretical amount of water and the reaction mixture is still homogeneous. Thus, the criticality of the use of an appropriate quantity of acid is evident in order to obtain an acceptable reaction time.

EXAMPLE 3

Still using the same apparatus described in EXAMPLE 1, the flask is charged with 71.3 grams of DHAD and 2.1 grams of 85% phosphoric acid (2.9% by wt. relative to DHAD). The mixture is heated and after 14 hours, only ⅔ of the theoretically expected amount of water has been distilled and the reaction mixture is still homogeneous. The criticality of the quantity of acid employed relative to the reaction time is further evident.

EXAMPLE 4

A 250-ml flask equipped with thermometer and dropping funnel and containing 7 grams of phosphoric acid (85%), a magnetic stirrer and the conventional apparatus for distilling off water as it is being formed, is charged with 70 grams of DHAD. The DHAD is melted by electric heating and brought to 160° C., whereafter the phosphoric acid is poured into the reaction vessel. A temperature drop in the reactor is immediately observed, together with the prompt evolution of water. The reaction is completed after 70 minutes. The yield is 66% molar of 2,5-dimethyl-2,4-hexadiene, the conversion is 100% molar and the selectivity towards 2,5-dimethyl-2,4-hexadiene is 66% molar.

EXAMPLE 5

A one-liter flask, equipped with glass-paddled stirrer, thermometer and dropping funnel is charged with 340 grams of DHAD, and 34 grams of 85% phosphoric acid is introduced into the funnel. The flask is then placed in a thermostatic bath which is initially adjusted to 179° C.–180° C.

As soon as the temperature of the melted DHAD reaches 155° C.–160° C., the 85% phosphoric acid is introduced into the flask. During the subsequent dehydration reaction, the temperature is in a range between the initial 155° C. and 118° C. After approximately 15 hours the theoretical amount of water has been distilled. Yield 67% molar of 2,5-dimethyl-2,4-hexadiene. Conversion 100% molar and selectivity 67% molar.

EXAMPLE 6

A 500-ml flask, electrically heated and equipped with a gloss-paddled stirrer, a thermometer and a Marcusson head with bubble condenser is charged, all at the same time, with 136 grams of DHAD, 13.6 grams of 85% phosphoric acid and 150 mls of vaseline oil. The mixture is refluxed and the theoretical amount of water is collected in 3 hours. 2,5-dimethyl-2,4-hexadiene is separated from the vaseline oil by distillation and the yield is 69% molar of 2,5-dimethyl-2,4-hexadiene, the conversion is 100% molar and the selectivity is 69% molar.

EXAMPLE 7

An electrically heated 250-ml flask, equipped with a mechanical stirrer, a thermometer and a Marcusson head with bubble condenser is charged with 100 grams of DHAD and 10 grams of 99% phosphoric acid and this mixture is refluxed. Within approximately 400 minutes the theoretical amount of water is distilled off. Yield 67% molar of 2,5-dimethyl-2,4-hexadiene, conversion 100% molar and selectivity 67% molar.

EXAMPLE 8

Using the same apparatus described in EXAMPLE 7, there are charged thereto grams 67.6 grams of DHAD and 6.8 grams of polyphosphonic acid. The reaction mixture is refluxed and the theoretical amount of water is distilled off in 170 minutes. The yield is 55% molar of 2,5-dimethyl-2,4-hexadiene, the conversion is 100% molar and the selectivity is 55% molar.

EXAMPLE 9

A 5-liter flask equpped with a Marcusson head with bubble condenser is charged with 2500 grams of DHAD, 250 grams of 85% phosphoric acid and 5 grams of 2,5-ditert.butyl hydroquinone. The reaction mixture is brought to a boil and after about 15 hours a virtually theoretical amount of water is collected. The raw product of the reaction is processed as usual. There is obtained a yield of 80% molar (conversion 100% molar) of 2,5-dimethyl-2,4-hexadiene. The raw product is subjected to distillation under atmospheric pressure. By utilizing a 20-plate column, it is possible to obtain 2,5-dimethyl-2,4-hexadiene having a purity over 99% (b.p. 136° C.-136.5° C.).

EXAMPLE 10

A one-liter flask equipped with glass paddled stirrer, thermometer, Marcusson head with bubble condenser and jacketed dropping funnel, is charged with 15 grams of 85% phosphoric acid and 1.5 g of 2,5-ditert. butyl hydroquinone whereas the dropping funnel is charged with 292 grams (2 mols) of DHAD and 1.5 g of 2,5-ditert. butyl hydroquinone. While the DHAD is melted in the jacketed funnel, an oil bath is heated to 175° C.–179° C. The flask is immersed in the oil bath, after which the DHAD is fed thereto over 60 minutes. During feed, the temperature is maintained at about 115° C. and on completion of the addition of the DHAD the mixture is further heated for 10 additional minutes, during which time, the temperature in the flask rises to 118° C. The reaction mixture is then cooled and processed in the usual way. The yield of 2,5-dimethyl-2,4-hexadiene is 70% molar, the conversion is 100% molar and the selectivity is 70% molar (mls of distilled water during reaction=65).

EXAMPLE 11

Using the same apparatus described in EXAMPLE 10, the flask is charged with 17.3 grams of 75% phosphoric acid and 1.5 grams of 2,5-ditert.butyl hydroquinone and the dropping funnel is charged with 292 grams (2 mols) of DHAD and 1.5 grams of 2,5-ditert.butyl hydroquinone. While the DHAD is melted in the jacketed funnel, an oil bath is heated to 175° C.–179° C. The flask is immersed in the oil bath, after which the DHAD is fed thereto over 85 minutes. During the feed, the temperature is maintained at about 110° -117° C. On completion of the addition of the DHAD, the mixture is further heated for 20 additional minutes, during time which the temperature of the flask rises to 118° C. The reaction mixture is then cooled and processed in the usual way. The yield of 2,5-dimethyl-2,4-hexadiene is 65% molar, the conversion is 100% molar and the selectivity is 65% molar (mls of water distilled off during the reaction=63).

EXAMPLE 12

Using the same apparatus as described in EXAMPLE 10, the flask is charged with 15.3 grams of 85% phosphoric acid and 0.3 grams of hydroquinone, and the funnel is charged with 292 grams (2 mols) of DHAD. While the DHAD is melted in the jacketed funnel, an oil bath is heated to 180° C. The flask is immersed in the oil bath, DHAD is fed after which the thereto over a period of 113 minutes. During feed, the temperature is maintained at about 118° C.–122° C. The reaction mixture is further heated for 10 additional minutes and processed in the usual way. The yield of 2,5-dimethyl-2,4-hexadiene is 66% molar, the conversion is 100% molar and the selectivity is 66% molar.

EXAMPLE 13 (a comparative Example)

A one-liter flask equipped with a bubble condenser, thermometer, magnetic stirrer is charged with 320 grams of DHAD and 32 grams of 85% phosphoric acid. Reflux is started and, in this apparatus, the water possibly formed by dehydration of the DHAD is not removed, but remains within the reaction environment. After 11 hours the mixture is cooled, the organic phase is separated from the water, dried over anhydrous sodium carbonate and analyzed. The mixture is essentially composed of tetramethyltetrahydrofuran (about 70% by wt), 7% of 2,5-dimethyl-2,4-hexadiene, and 10% of an unsaturated alcohol having a mol. wt 128, derived from the DHAD by the loss of one molecule of water.

We claim:

1. A process for the preparation of 2,5-dimethyl-2,4-hexadiene comprising the steps of contacting 2,5-dimethyl-2,5-hexanediol in liquid phase or in aqueous solutions thereof with an acid, derivatives of said acid or substances which form free acids, heating the mixture thus obtained to a temperature in a range of from about 100° C. to about 160° C., distilling off water as it is formed, recycling the organic phase, and separating the 2,5-dimethyl-2,4-hexadiene obtained from the reaction mixture.

2. Process according to claim 1 wherein the mixture is heated to a temperature in a range of from about 100° C. to about 140° C.

3. Process according to claim 1 wherein the reaction is carried out at a pressure in a range of from about 1 to about 10 bars.

4. Process according to claim 1 wherein the acid is selected from the group consisting of phosphoric acid, polyphosphoric acid, phosphorous pentoxide, sulfuric acid, boric acid, hydrobromic acid, potassium sulfate, oxalic acid and toluenesulfonic acid.

5. Process according to claim 1 wherein the acid is selected from the group consisting of polyphosphoric acid and phosphoric acid having a concentration in a range of from about 75% to about 99%.

6. Process according to claim 1 wherein the acid is employed in an amount in a range of from about 1% to about 50% by weight relative to the 2,5-dimethyl-2,5-hexanediol.

7. Process according to claim 1 wherein the acid is employed in an amount in a range of from about 3% to about 30% by weight relative to the 2,3-dimethyl-2,5-hexanediol.

* * * * *